(12) United States Patent
Ferko, IV

(10) Patent No.: US 7,875,281 B2
(45) Date of Patent: Jan. 25, 2011

(54) COMPOSITION AND METHOD FOR REPELLING MOLES, VOLES AND GOPHERS

(75) Inventor: George J. Ferko, IV, Palmerton, PA (US)

(73) Assignee: Liquid Holding Co., Inc., Brodheadsville, PA (US)

( * ) Notice: Subject to any disclaimer, the term of this patent is extended or adjusted under 35 U.S.C. 154(b) by 564 days.

(21) Appl. No.: 12/012,686

(22) Filed: Feb. 4, 2008

(65) Prior Publication Data

US 2008/0132572 A1 Jun. 5, 2008

Related U.S. Application Data

(63) Continuation of application No. 11/125,678, filed on May 10, 2005, now Pat. No. 7,384,647.

(51) Int. Cl.
*A01N 25/02* (2006.01)

(52) U.S. Cl. ............. 424/405; 424/409; 424/731; 514/558; 514/920

(58) Field of Classification Search .............. None
See application file for complete search history.

(56) References Cited

U.S. PATENT DOCUMENTS

| 4,016,296 A | 4/1977 | DeSantis |
| 5,658,954 A | 8/1997 | Targosz |
| 6,395,776 B1 | 5/2002 | Losel et al. |
| 2002/0076428 A1 | 6/2002 | Wharton |
| 2005/0276834 A1 | 12/2005 | Martin et al. |

*Primary Examiner*—Neil Levy
(74) *Attorney, Agent, or Firm*—Maryellen Feehery Hank; Reed Smith LLP

(57) ABSTRACT

The present invention is a composition and method for repelling moles, voles, gophers, chipmunks and armadillos by applying a composition comprising castor oil, yellow grease and sodium lauryl sulfate to plant materials.

5 Claims, No Drawings

COMPOSITION AND METHOD FOR REPELLING MOLES, VOLES AND GOPHERS

This application is a continuation application of U.S. application Ser. No. 11/125,678, filed on May 10, 2005, now U.S. Pat. No. 7,384,647, which is hereby incorporated by reference in its entirety.

BACKGROUND OF THE INVENTION

Moles, voles, gophers and other burrowing animals can wreak havoc on lawns and gardens. Numerous products in the prior art have been developed to repel these burrowing animals with only moderate success. While the prior art recognizes that castor oil is a repellent for moles, voles and gophers, the problem is that when castor oil is administered in the prior art, it is diluted with water, often in a hose spray. If the water is cool, the castor oil gels (castor oil freezes at about 60-65° F.). (All temperatures given in this specification are given in Fahrenheit, unless otherwise noted.) The gel clogs the holes of the sprayer and then the repellent is not delivered to the desired area.

Some castor oil products in the prior art require that the vial containing the castor oil be placed in a warm bath before using if the water is cool. However, this only helps until the castor oil and/or water cools and the castor oil gels again. Other products combine soybean oil with castor oil, but there is still a gelling problem.

Therefore, the industry has a need for an effective repellent for moles, voles, gophers and other burrowing animals, which is not limited by the gelling of castor oil. Preferably, the repellent should not be harmful to the animals, or the surroundings on which the repellent is deposited.

SUMMARY OF THE INVENTION

According to the present invention, the temperature at which the repellent composition containing castor oil gels is lowered significantly, thus preventing gelling when being applied to the desired areas. When the composition is a liquid, plant materials and soil in infested or expected-to-become infested areas are wet with the composition.

One embodiment of the present invention comprises castor oil, edible fats and oils and sodium lauryl sulfate. The composition may be provided in a concentrate (which will be diluted with water before use) or ready to use, or in a solid form (for example, without limitation, where a liquid was deposited on solids, e.g. without limitation granules, particulates, and crushed egg shells and then the solids are spread around the infested or expected-to-become infested areas).

It is preferred that the composition be liquid because the liquid is then deposited on plant materials. Target animals then ingest the composition (directly or indirectly). Voles and gophers eat these plant materials, while moles eat earthworms, grubs and other animals which have eaten the plant material coated with the composition. Without being limited by mechanism, the repellent eliminates food sources for the targeted animals. After ingestion of the plant material (for the voles and gophers) and the animals who ate the plant material (for the moles), target animals (e.g. without limitation moles, voles and gophers) suffer gastrointestinal disruption and if these animals continually ingest such food, they will starve. However, it is believed that after one or several such disruptions, the target animals would relocate (and thus be repelled from the specified area). These target animals, (e.g. without limitation small animals) have extremely high metabolisms and a continual interruption of food sources causes immediate behavioral changes or death.

"Target animals" means the animals sought to be repelled by the composition. Target animals include but are not limited to any animal that cannot digest ricinoleic acid, such as moles, voles, gophers, chipmunks, and armadillos. Such ricinoleic acid may be on the food source itself or ingested by the food source (e.g., without limitation, earthworms may eat the coated plant material and are not repelled but the moles that eat the earthworms are repelled through their inability to digest ricinoleic acid.)

"Plant materials" means any part of the plant, above or below the soil, including but not limited to the leaves, stems and roots. In one embodiment, the composition may be applied to plant material below the soil by wetting the soil.

Ricinoleic acid means the hydroxy fatty acid, ricinoleic acid ($C_{18}H_{34}O_3$). Isoricinoleic acid may also be used in the present invention. Castor oil contains a high amount of ricinoleic acid, and a lesser amount of isoricinoleic acid. Cold pressed castor oil is a preferred ingredient, due to its high concentration of ricinoleic acid.

DETAILED DESCRIPTION OF THE INVENTION

The present invention, in one embodiment, comprises about 66.00% castor oil, about 26.00% edible fats and oils, and about 8.00% sodium lauryl sulfate. All percentages given in this specification are given as weight percentages, unless otherwise noted. The percentages are also given as percentages of the total composition, unless otherwise noted. This is a simple mixture, which is very miscible with water even at temperatures as low as the low 30's.

In one embodiment, the present invention comprises about 45% to about 75% castor oil, about 10% to about 36% edible fats and oils, and about 2% to about 14% alkyl sulfates, preferably without limitation about 2% to about 14% sodium lauryl sulfate. This composition, and all of the composition embodiments of the present invention, may then be diluted with water before it is administered.

Another embodiment is set forth in Table 1. This embodiment may be applied with a hose sprayer, and thereby diluted and distributed with water. Preferably, the composition is mixed with water first (v/v ratios of composition to water from about 1:8 to about 1:250, preferably about 1 ounce of composition to about 1 gallon of water.) After liberally applying the mixed composition, the area should be soaked with water, but not overwatered. If the infestation is high or if substantial rainfall occurs, the mixture may need to be reapplied. 1 quart of composition, which is then mixed with water, covers approximately 10,000 square feet.

TABLE 1

| Component | Manufacturer | Weight % |
| --- | --- | --- |
| Castor Oil | Univar | 66.00 |
| Edible Fats and Oils (Yellow Grease) | R. E. Ebersole | 26.00 |
| Sodium Lauryl Sulfate | Univar | 8.00 |

"Edible fats and oils" means vegetable oils with an iodine value of between about 84-130, saponification value of about 170-193, solidification range of fatty acids of about 2-10° C., and hydroxyl values of 145-170. A preferred "edible fats and oils" is yellow grease, which qualifies under the FIFRA exempt status. Yellow grease may be recovered from spent deep fryers in the restaurant industry; it may contain any number of vegetable oils. As seen in yellow grease for example, the edible fats and oils may be recycled from other uses and maybe a mixture of different types of fats and/or oils.

An iodine value is the amount of iodine in grams needed to saturate 100 ml of the oil. The higher the iodine value, the more unsaturated the oil is; oils with high iodine values resist gelling better than oils with low Iodine Values, which tend to be solid at room temperature.

A saponification value is the measure of the mean molecular weight of the component glycerides, or fatty acids, and is defined as the amount of mg of potassium hydroxide required to saponify 1 g of oil.

Another embodiment of the present invention is a composition comprising ricinoleic acid, edible fats and oils and one or more alkyl sulfate, preferably without limitation sodium lauryl sulfate. This composition may further comprise isoricinoleic acid.

Another embodiment of the present invention is a composition comprising isoricinoleic acid, edible fats and oils and one or more alkyl sulfates.

The addition of edible fats and oils and alkyl sulfates, e.g. sodium lauryl sulfate, to the castor oil effectively lowers the solidification range of the mixture to about 5° C. or less, eliminating the gelling problems noted in the prior art. Sodium lauryl sulfate also slightly increases the water solubility of the edible fats and oils and the castor oil, allowing (without being limited to mechanism) deeper soil penetration and better root protection (via better coverage of the roots, repelling the target animals).

Sodium lauryl sulfate is an alkyl sulfate of the formula: $CH_3(CH_2)_{18}CH_2OSO_3Na$. Other alkyl sulfates may be effective to increase the water solubility of the edible fats and oils and the castor oil, and lowering the solidification range of the composition by at least about 10° C., preferably, without limitation, to about 5° C. or less.

In other embodiments, it may be desirable to add additional components to the compositions, such as plant fertilizers, plant growth stimulants, repellents for other animals, repellents for insects, colorants, preservatives, dyes, and perfumes.

A composition comprising ricinoleic acid, edible fats and oils and one or more alkyl sulfates may be applied to plant material in an area infested with or likely to become infested with target animals, especially one or more of the following: moles, voles, gophers, chipmunks and armadillos, in order to repel the target animals. The composition may be solid or preferably liquid. A hose sprayer may be used to dilute and distribute the composition and to wet the soil, so that roots may be coated by the composition as well as the plant material above the soil.

It is to be understood that while the invention has been described in conjunction with the detailed description thereof, that the foregoing description is intended to illustrate and not limit the scope of the invention, which is defined by the scope of the appended claims. Other aspects, advantages, and modifications are evident from a review of the following claims.

The invention claimed is

1. A method for repelling target animals comprising
applying a composition comprising
about 45% to about 75% castor oil,
about 10% to about 36% yellow grease having an iodine value about 84 to about 130, a saponification value of about 170- about 193, a solidification range of fatty acids of about 2- about 10° C., and a hydroxyl value of about 145- about 170, and
about 2% to about 14% sodium lauryl sulfate
to plant material in an area inhabited by one or more target animals selected from the group consisting of moles, voles, gophers, chipmunks and armadillos, wherein the percentages are weigh percentages of the total composition and wherein the composition is liquid.

2. The method of claim 1 wherein the target animals are moles.

3. The method of claim 1 wherein the target animals are voles.

4. The method of claim 1 wherein the target animals are gophers.

5. A method for repelling target animals comprising
applying a composition comprising ricinoleic acid, edible fats and oils having an iodine value about 84 to about 130, a saponification value of about 170- about 193, a solidification range of fatty acids of about 2- about 10° C., and a hydroxyl value of about 145- about 170, and one or more alkyl sulfate to plant material in an area inhabited by one or more target animals selected from the group consisting of moles, voles, gophers, chipmunks and armadillos, wherein the ricinoleic acid is present as a component which makes up about 45% to about 75% of the composition, the edible fats and oils make up about 10% to about 36% of the composition, and the alkyl sulfates make up about 2% to about 14% of the composition, wherein the composition is a liquid.

* * * * *